United States Patent
Shoeb

(10) Patent No.: US 10,004,427 B1
(45) Date of Patent: Jun. 26, 2018

(54) METHODS, SYSTEMS, AND DEVICES FOR DETERMINING A RESPIRATION RATE

(71) Applicant: Verily Life Sciences LLC, Mountain View, CA (US)

(72) Inventor: Ali Shoeb, Mill Valley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 165 days.

(21) Appl. No.: 14/817,951

(22) Filed: Aug. 4, 2015

(51) Int. Cl.
| | |
|---|---|
| *A61B 5/08* | (2006.01) |
| *A61B 5/00* | (2006.01) |
| *A61B 5/087* | (2006.01) |

(52) U.S. Cl.
CPC .......... *A61B 5/0803* (2013.01); *A61B 5/0816* (2013.01); *A61B 5/0871* (2013.01); *A61B 5/681* (2013.01); *A61B 5/742* (2013.01)

(58) Field of Classification Search
CPC ... A61B 5/0803; A61B 5/0816; A61B 5/0871; A61B 5/681; A61B 5/742
See application file for complete search history.

(56) References Cited

U.S. PATENT DOCUMENTS

| | | | | |
|---|---|---|---|---|
| 8,954,135 B2* | 2/2015 | Yuen | ...................... | H04W 4/027 |
| | | | | 600/407 |
| 2007/0299323 A1* | 12/2007 | Arns | .................... | A61B 5/0059 |
| | | | | 600/301 |
| 2013/0079606 A1 | 3/2013 | McGonigle et al. | | |
| 2013/0079647 A1 | 3/2013 | McGonigle et al. | | |
| 2013/0079656 A1 | 3/2013 | Dripps et al. | | |
| 2013/0079657 A1 | 3/2013 | Ochs et al. | | |
| 2014/0275889 A1 | 9/2014 | Addison et al. | | |
| 2014/0276175 A1 | 9/2014 | Banet et al. | | |
| 2015/0208964 A1* | 7/2015 | Addison | ............ | A61B 5/14551 |
| | | | | 600/324 |

OTHER PUBLICATIONS

Li et al., "Comparison of respiratory-induced variations in photoplethysmographic signals", Physiol. Meas. 31 (2010), pp. 415-425.

(Continued)

*Primary Examiner* — Amanda Patton
(74) *Attorney, Agent, or Firm* — McDonnell Boehnen Hulbert & Berghoff LLP

(57) ABSTRACT

Disclosed are methods, systems, and devices for determining a respiration rate. An example method includes capturing by a wearable device over a non-zero time period a PPG signal and making a first determination that, during the non-zero time period, the wearable device has moved less than a threshold amount. Responsive to the first determination, the method includes (i) determining from the PPG signal each of (1) a respiratory-induced intensity variation (RIIV) signal, (2) a respiratory-induced amplitude variation (RIAV) signal, and (3) a respiratory-induced frequency variation (RIFV) signal; and (ii) making a second determination that, based on the RIIV signal, the RIAV signal, and the RIFV signal, a respiration rate is determinable. Responsive to the second determination, the method includes (i) determining the respiration rate and (ii) providing by the wearable device a notification, with the notification being based at least in part on the determined respiration rate.

18 Claims, 10 Drawing Sheets

(56) References Cited

OTHER PUBLICATIONS

Scholkmann et al., "An Efficient Algorithm for Automatic Peak Detection in Noisy Periodic and Quasi-Periodic Signals", Algorithms 2012, 5, pp. 588-603.
Karlen et al., "Multiparameter Respiratory Rate Estimation From the Photoplethysmogram", IEEE Transactions on Biomedical Engineering, vol. 60, No. 7, Jul. 2013.

* cited by examiner

METHODS, SYSTEMS, AND DEVICES FOR DETERMINING A RESPIRATION RATE

BACKGROUND

Unless otherwise indicated herein, the materials described in this section are not prior art to the claims in this application and are not admitted to be prior art by inclusion in this section.

One method for determining a heart rate of a person involves using a photoplethysmographic (PPG) sensor. Such a sensor typically includes one or more light sources and one or more detector. During use, the one or more lights sources may illuminate a portion of a person's skin. Blood flowing through vessels within the illuminated portion of the skin reflects a portion of the emitted light, which the one or more detectors may detect over a non-zero time period, thereby providing a PPG signal. A pulse or heart rate can thus be determined from the PPG signal, as changes in the intensity of the detected light that correlate to changes in blood flow through the illuminated area resulting from the person's heart pumping blood. However, a number of factors may affect the intensity of the light detected by the one or more detectors. For instance, a person's breathing may cause respiratory-induced variations in a PPG signal. Assuming a regular respiration rate over the non-zero time period in which a given PPG signal is captured, it may be possible to estimate a respiration rate from one or more respiratory-induced variations in the PPG signal.

SUMMARY

In one aspect, a method is disclosed. The method includes capturing by a wearable device over a non-zero time period a photoplethysmographic (PPG) signal. The method also includes making a first determination that, during the non-zero time period, the wearable device has moved less than a threshold amount. Responsive to the first determination, the method includes (i) determining from the PPG signal each of (1) a respiratory-induced intensity variation (RIIV) signal, (2) a respiratory-induced amplitude variation (RIAV) signal, and (3) a respiratory-induced frequency variation (RIFV) signal; and (ii) making a second determination that, based on at least two of the RIIV signal, the RIAV signal, and the RIFV signal, a respiration rate is determinable. Responsive to the second determination, the method includes (i) determining, from at least two of the RIIV signal, the RIAV signal, and the RIFV signal, the respiration rate and (ii) providing by the wearable device a notification, with the notification being based at least in part on the determined respiration rate.

In another aspect, a wearable device is disclosed. The wearable device includes a sensor configured to capture PPG signals, a processor, and a data storage having stored therein program instructions executable by the processor. The program instructions, when executed by the processor, cause the processor to receive from the sensor over a non-zero time period a PPG signal. The program instructions also cause the processor to make a first determination that, during the non-zero time period, the wearable device has moved less than a threshold amount. Additionally, the program instructions cause the processor to, after making the first determination, (a) determine from the PPG signal each of (1) an RIIV signal, (2) an RIAV signal, and (3) an RIFV signal; and (b) make a second determination that, based on at least two of the RIIV signal, the RIAV signal, and the RIFV signal, a respiration rate is determinable. Further, the program instructions cause the processor to, after making the second determination, determine a respiration rate based on the RIIV signal, the RIAV signal, and the RIFV signal.

In still another aspect, a system is disclosed. The system comprises means included in a wearable device for capturing over a non-zero time period a PPG signal. The system further comprises means for making a first determination that, during the non-zero time period, the wearable device has moved less than a threshold amount. The system further comprise means for, after making the first determination, (i) determining from the PPG signal each of (1) an RIIV signal, (2) an RIAV signal, and (3) an RIFV signal; and (ii) making a second determination that, based on at least two of the RIIV signal, the RIAV signal, and the RIFV signal, a respiration rate is determinable. Additionally, the system comprises means for, after making the second determination, (i) determining, from at least two of the RIIV signal, the RIAV signal, and the RIFV signal, the respiration rate and (ii) providing by the wearable device a notification, with the notification being based at least in part on the determined respiration rate.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Figure 1:
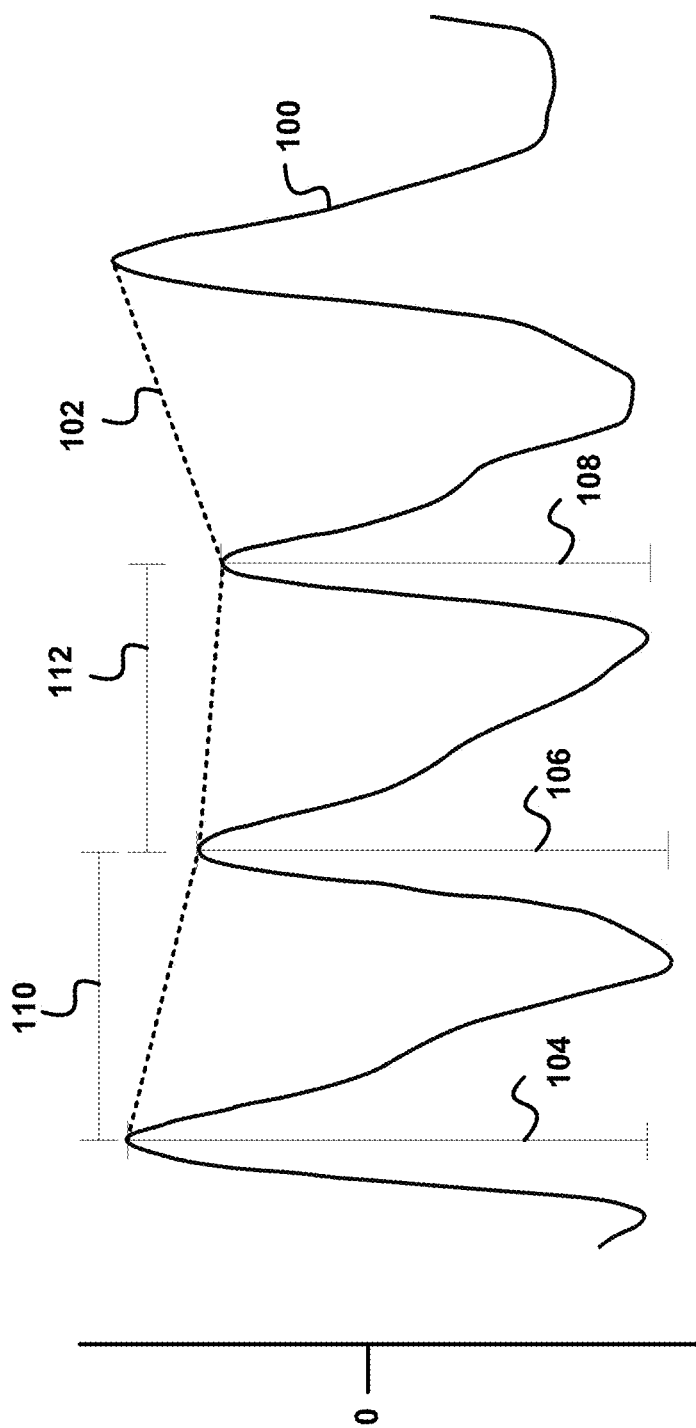
FIG. 1 is a graph of an example photoplethysmographic signal.

Example embodiments described herein are directed to aspect of methods, systems, and devices for determining a respiration rate from respiratory-induced variations (RIVs)

in a photoplethysmographic (PPG) signal. FIG. 1 illustrates three such RIVs in an example PPG signal 100: respiratory-induced intensity variations (RIIV), respiratory-induced amplitude variations (RIAV), and respiratory-induced frequency variations (RIFV). RIIVs are variations in perfusion baseline (e.g., the peak intensity of pulses) of a PPG signal that result from the intrathoracic pressure variations caused by the exchange of blood between the pulmonary circulation and the systemic circulation. Variations in the intensities of the pulses in the PPG signal 100, as shown by a trend line 102, are example RIIVs. In contrast, RIAVs are variations in the amplitudes of individual pulses that result from a decrease (or increase) in cardiac output due to reduced (or increased) ventricular filling. Differences in a first amplitude 104 of a first pulse, a second amplitude 106 of a second pulse, and a third amplitude 108 of a third pulse are example RIAVs. Finally, RIFVs are variations in pulse frequency caused by the autonomic response that synchronizes heart rate and respiration rate; in general, heart rate increases during inspiration and decreases during expiration. A difference between (1) a first time period 110 between the first pulse and the second pulse and (2) a second time period 112 between the second pulse and the third pulse is an example of an RIFV.

An example method includes capturing a by a wearable device over a non-zero time period a PPG signal and making a first determination that a wearable device has moved less than a threshold amount. Since a movement of the wearable device can adversely affect a PPG signal, thereby making any subsequent determination of the respiration rate potentially unreliable, making the first determination may reduce likelihood of determining an inaccurate respiration rate. An example wearable device may include a sensor configured to capture a PPG signal during each of a plurality of non-zero time periods. The wearable device may thus be configured to be worn on a part of a user's body that facilitates capturing PPG signals, such as the user's wrist. The wearable device may also include and/or be connected to one or more additional sensors configured to capture physiological and/or non-physiological parameters. Examples of such physiological parameters include a body temperature, a galvanic skin response, an insulin level, or the like, while the non-physiological parameters may include a movement of the wearable device, a position of the wearable device, an activity in which the user is engaging, etc.

The example method also includes, responsive to making the first determination, (i) determining from the PPG signal each of (1) an RIIV signal, (2) an RIAV signal, and (3) an RIFV signal; and (ii) making a second determination that, from at least two of the RIIV signal, the RIAV signal, and the RIFV signal, a respiration rate is determinable. The wearable device may make the second determination by processing the RIV signals to determine from each RIV signal a preliminary respiration rate. The wearable device may then make the second determination by determining that at least two of the three preliminary respiration rates are within a threshold of each other.

Alternatively, a remote computing device, such as a server or a server cluster, may make the second determination. By way of example, the wearable device may process the RIV signals to generate a vector that includes power levels in each of one or more frequency bands for each RIV signal. The wearable device may send the vector to the remote computing device, and the remote computing device may use a machine-learning algorithm to determine from the vector whether the respiration rate is determinable. The remote computing device may then send to the wearable device a signal indicative of whether the respiration rate is determinable.

Responsive to making the second determination, the example method then includes (i) determining from two or more of the RIV signals the respiration rate and (ii) causing by the wearable device an output device to provide a notification, with the notification being based on the determined respiration rate. As used herein, a notification refers to a tactile output, an audible output, a visual output, or another type of perceptible output that a user of the wearable device, and possibly another person or animal (e.g., a service animal) in the vicinity of the user, can perceive. The wearable device may perform one or more statistical operations to determine the respiration rate. By way of example, the wearable device could determine the respiratory by determining a cross-correlation of two or more RIV signals, or the wearable device could determine the respiration rate by averaging two or more of the preliminary respiration rates. Alternatively, the remote computing device could determine from the vector the respiration rate and send to the wearable device a signal that includes data indicative of the respiration rate.

Beneficially, the methods, systems, and devices described herein may provide a user of a wearable device with an efficient and reliable way to determine the user's respiration rate. Additionally, the determined respiration rate may allow a user, or perhaps a user's physician or other attending medical professional, to determine whether the user shows respiratory symptoms indicative of certain medical conditions. The wearable device and/or the remote computing device may have access to data indicative of the respiration rates and/or trend in respiration rates, as well as other physiological parameters and non-physiological parameters, that correlate to various medical conditions. The wearable device and/or remote computing device may access such data to determine whether the respiration rates and other physiological and non-physiological parameters determined or captured over a period of time correlates to a particular medical condition or set of medical conditions. For instance, a negligible respiration rate while the user is sleeping may indicate that the user suffers from a sleep disorder, such as sleep apnea, while a prolonged, excessive respiratory rating (greater than about 40 breaths per minute) may be indicative of a respiratory infection such as bronchitis or pneumonia. In the event a correlating set of data is identified, the notification may alert the user and/or medical professionals that the user shows symptoms of the identified medical condition.

II. EXAMPLE SYSTEMS AND SYSTEM COMPONENTS

Figure 2:
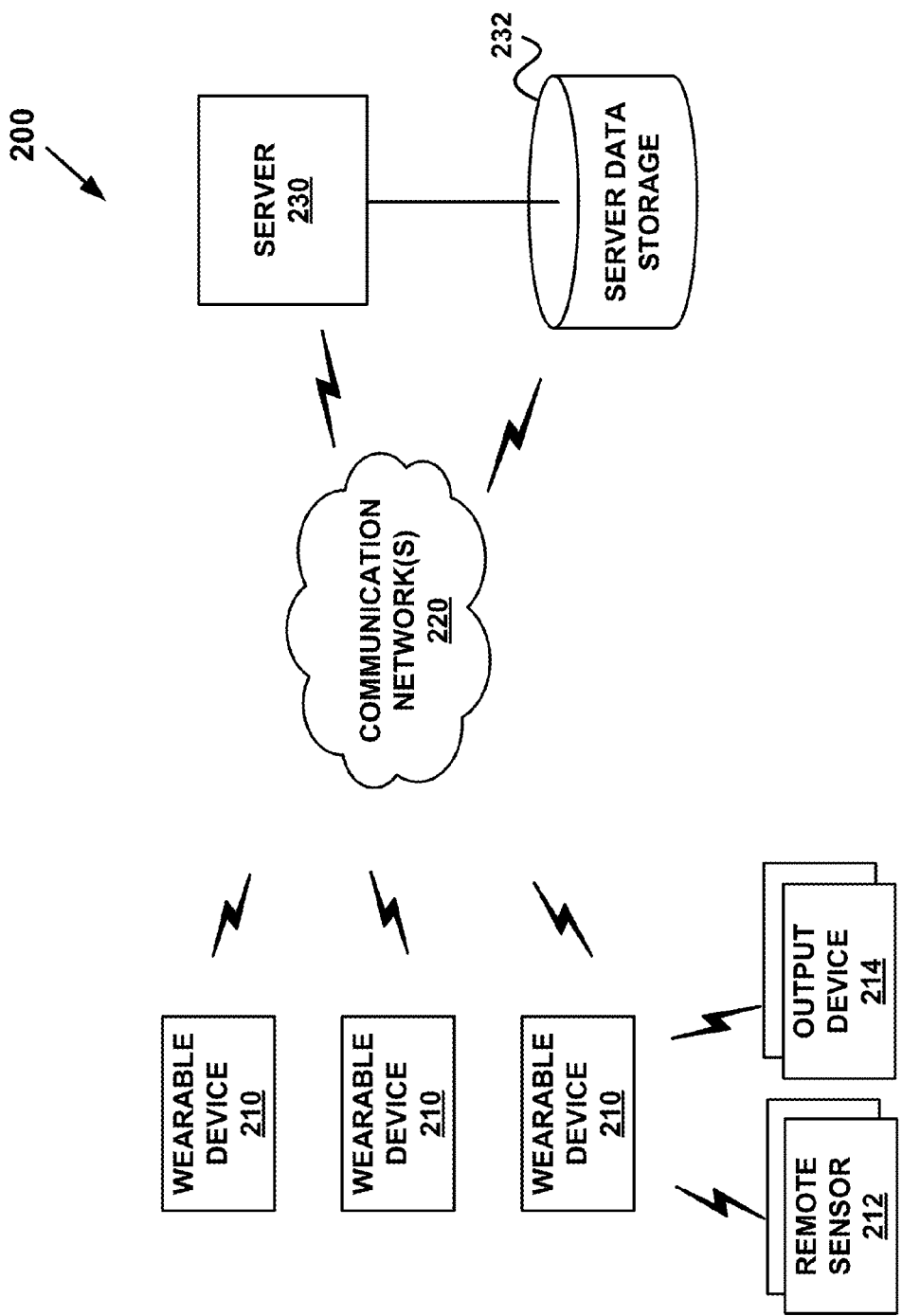
FIG. 2 is a block diagram of an example health monitoring system that includes a plurality of electronic devices in communication with a server.

Turning now to the figures, FIG. 2 is a simplified schematic of a health monitoring system 200 that includes wearable devices 220. A user may wear one of the wearable device 220 and possibly one or more remote sensors 212 that communicate with the user's wearable device 220. Each wearable device 220 may capture and/or receive from the sensor(s) 212 a plurality of physiological parameter measurements and a plurality of non-physiological para parameter measurements. The user's wearable device 210 may also communicate with one or more output devices 214, which may provide a notification. By way of example, the notification may be an audible, tactile, or visual, and the one or more output devices 214 may include smartphones, alarm clocks, tablet computers, or another electronic device capable of providing one or more notifications.

The wearable devices 210 may also communicate with a server 230 via a communication network 220, perhaps by a wireline connection and/or a wireless connection. The communication network 220 may include one or more of a plain old telephone service (POTS) network, a cellular network, a fiber-optic network, or a data network. The server 230 may communicate with the wearable devices 210 according to one or more network protocols and/or application-level protocols to facilitate the use of network-based or cloud-based computing on client devices. The server 230 may include integrated data storage (e.g., memory, disk drives, etc.) and may also be able to access a separate server data storage 232. Communication between the server 230 and the server data storage 232 may be direct (e.g., via a wireline or via a local wireless communication link) and/or via the communication network 220. The server data storage 232 may store application data that is used to facilitate the operations of applications performed by the wearable devices 210 and/or the server 230.

Additionally or alternatively, the server 230 and the server data storage 232 may store applications and application data at one or more places accessible via communication network 220. These places may be data centers containing numerous servers and storage devices. The exact physical location, connectivity, and configuration of the server 230 and the server data storage 232 may be unknown and/or unimportant to client devices (e.g., the wearable devices 210). Accordingly, the server 230 and the server data storage device 232 may be referred to as "cloud-based" devices that are housed at various remote locations. One possible advantage of such "cloud-based" computing is to offload processing and data storage from client devices, thereby simplifying the design and requirements of these client devices.

In some embodiments, the server 230 and the server data storage 232 may be a single computing system residing in a single data center. In other embodiments, the server 230 and the server data storage 232 may include multiple computing systems in a data center, or even multiple computing systems in multiple data centers, where the data centers are located in diverse geographic locations. For example, FIG. 2 depicts each of the server 230 and the server data storage device 232 as potentially residing in different physical locations.

In addition to receiving communications from the wearable devices 210, such as data indicative of physiological and non-physiological parameter measurements, the server 230 may also be configured to gather and/or receive, from either each wearable device 210 or some other source(s) (not shown), information regarding a user's overall medical history, environmental factors and geographical data. For example, the server 230 and/or the server data storage 232 may include a user account for every user that contains the user's medical history.

Moreover, in some examples, the server 230 may be configured to regularly receive other information, such as viral illness or food poisoning outbreak data from the Centers for Disease Control (CDC) and weather, pollution and allergen data from the National Weather Service. Further, the server 230 may be configured to receive data regarding a user's health state from a hospital or physician. Such information may be used in a machine-learning algorithm implemented by the server 230, which may identify vectors of physiological and/or non-physiological parameters corresponding to various medical conditions.

Additionally, the server 230 may be configured to gather and/or receive the date, time of day and geographical location of each wearable device 210 during each measurement period. In measuring physiological parameters of the user (e.g., extracted PPG waveforms), such information may be used to detect and monitor spatial and temporal spreading of diseases, which may be used to assess whether the user has a respiratory illness. As such, the wearable devices 210 may be configured to determine and/or provide an indication of its own location. For example, an electronic device may include a GPS system so that it can include GPS location information (e.g., GPS coordinates) in a communication to the server. As another example, a wearable device may use a technique that involves triangulation (e.g., between base stations in a cellular or Bluetooth® network) to determine its location. Other location-determination techniques are also possible. Such information may be useful in distinguishing parameters and data the correlate to a medical condition from parameters and data that correspond to physical activity, for example.

Further, some embodiments of the system may include privacy controls which may be automatically implemented or controlled by the user of each wearable device 210. For example, where a user's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, the user of each wearable devices 210 may be provided with an opportunity to control whether or how the wearable device 210 collect information about the user (e.g., information about a user's medical history, social actions or activities, profession, a user's preferences, or a user's current location), or to control how such information may be used. Thus, the user may have control over how information is collected about him or her and used by a clinician or physician or other user of the data. For example, a user may elect that data, such as health state and physiological parameters, collected from his or her device may only be used for generating an individual baseline and recommendations in response to collection and comparison of his or her own data and may not be used in generating a population baseline or for use in population correlation studies.

Although only three wearable devices 210, one server 230, and one server data storage 232 are shown in FIG. 2, remote health monitoring system 200 may include any number of each of these components. For instance, the health monitoring system 200 may include thousands of electronic devices, thousands of servers, and/or thousands of server data storages. Further, while FIG. 2 depicts only one wearable device 210 as being connected to the remote sensors(s) 212 and the output device(s) 214, each wearable device 210 in the remote health monitoring system 200 may be connected to one or more sensors and/or output devices.

In line with the discussion above, a user may wear one of the wearable devices 210 and interact with the wearable devices 210 to determine the user's respiration rate. Alternatively, the wearable devices 210 may automatically determine a respective user's respiration rate under certain conditions, such as when the wearable device is substantially stationary. In another example, the wearable devices 210 may exchange data with the server 230 via to determine a respiration rate. In some examples, the wearable devices 210 and/or the server 230 may be configured to provide a notification of a preliminary diagnosis of a medical condition from which a given user of one of the wearable devices 210 suffers.

In one example operation, the server 230 may receive from the wearable devices 210 a plethora of physiological parameter measurements and non-physiological parameter measurements measured over a one or more non-zero time intervals, such as time intervals of about 20 seconds. Whereas the physiological parameter measurements may include PPG signals, galvanic skin measurements, and/or skin temperatures, the non-physiological parameter measurements may include measurements indicative of movements of the wearable device 210 and/or audio recordings.

From the received plethora of physiological parameter measurements and non-physiological parameter measurements, the server 230 may implement a machine-learning algorithm to determine vectors of parameters that correlate to a respiration rate. To this end, the machine-learning algorithm may be trained with the received physiological parameter measurements and non-physiological parameter measurements, with the physiological parameter measurements including at least a baseline respiration rate and respiratory data extracted from PPG signals. A baseline respiration rate may be determined by counting a number of breaths during a given non-zero time period, or the baseline respiration rate may be determined using another electrical or electromechanical device. The server 230 may receive from the wearable device 210 a plurality of sets of RIV signals, with each set or RIV signals including an RIAV signal, and RIIV signal, and an RIFV signal. For each set of RIV signals, the server 230 may determine from the respective RIV signals an preliminary respiration rate, and combine the preliminary respiration rates if at least two of the preliminary respiration rates are within a threshold of each other. Alternatively, statistical methods may be used to combine the RIV signals in each set, perhaps by determining cross-correlations. Each combined RIV signal may then be weighted based on a variance of each combined RIV signals to a respective baseline respiration rate. The machine-learning algorithm may be further trained using a training algorithm, such as a k nearest neighbor (KNN) algorithm (with k being a positive integer, for instance, seven).

Further, the machine-learning algorithm may be trained to determine sets of vectors that correlate to one or more respiratory or other health conditions. The vector for a given condition may include ranges and/or thresholds for one or more physiological parameters and one or more non-physiological parameters. The server 230 may then send the determined sets of vectors to the wearable devices 210. Additionally or alternatively, the server 230 may receive from the wearable devices 210 one or more sets of vectors, with each vector including data indicative of one or more physiological and/or non-physiological parameters. The server 230 may determine a respiration rate from each received vector and may send data indicative of each determined respiration rate to the respective wearable device 210. Moreover, the server 230 may determine that the vector, or perhaps a series of consecutive vectors correlating to data captured over a longer non-zero time period (e.g., several minutes, hours, or days) is indicative of a user having symptoms of a medical condition. In this example, the server 230 may send to a wearable device 210 or another computing device (e.g., a physician's computing device) via the network 220 an alert and/or signal indicative of the determined diagnosis, thereby facilitating verification and treatment of a medical condition (e.g., a respiratory infection) that the user of the wearable device 210 may have.

Figure 3:
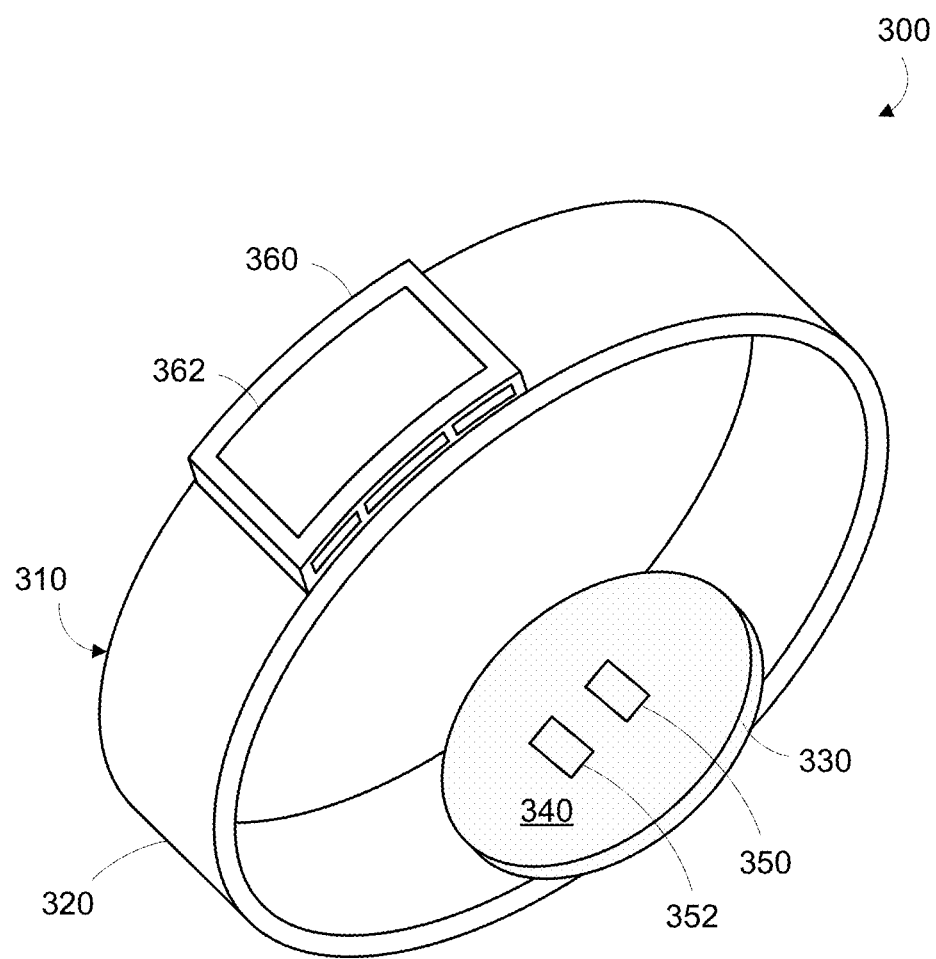
FIG. 3 is an example wearable electronic device.

Shown in FIG. 3 is a wearable device 300 that can automatically measure a plurality of physiological parameters of a person wearing the device. The term "wearable device," as used in this disclosure, refers to any device that is capable of being worn at, on or in proximity to a body surface, such as at a wrist, ankle, waist, chest, or other body part. In order to take in vivo measurements in a non-invasive manner from outside of the body, the wearable device 300 may be positioned on a portion of the body where subsurface vasculature is easily observable, the qualification of which will depend on the type of detection system used. A mount 310, such as a belt, wristband, ankle band, etc., can be provided to mount the wearable device 300 at, on, or in proximity to the body surface. The mount 310 may prevent the wearable device from moving relative to the body, thereby reducing measurement error and noise. The mount 310 could take the form of a strap or band 320 that the user wears around a body part. Further, the mount 310 may include an adhesive substrate for adhering the wearable device 300 to the user's body.

The measurement platform 330 may include one or more sensors configured to capture a measurement of at least one physiological parameter measurement. The at least one physiological parameter could be any parameter that may relate to the health of the person wearing the wearable device 300. For example, the wearable device 300 could be configured to measure blood pressure, pulse rate, respiration rate, skin temperature, Galvanic skin response, etc. The measurement platform 330 may thus be disposed on the mount 310 such that the measurement platform 330 is positioned on the body where subsurface vasculature is easily observable. When worn, an inner face 340 of the measurement platform 330 may face the body surface.

In one example, the sensor(s) may generate PPG signals from which the wearable device 300 may determine one or more physiological parameters. To this end, the measurement platform 330 may include on the inner face 340 a light emitter 350 and a light detector 352. Each PPG signal may include data indicative of detected light at one or more wavelengths, and the wearable device may be configured to determine values for one or more physiological parameters based on the intensity (or change in intensity) and wavelength of light received at the light detector 352. By way of example, the wearable device 300 may use the sensor to determine a heart rate, a heart rate variability, a respiration rate, a respiration rate variability, or the like.

In other examples, the measurement platform 330 may include one or more additional sensors, each of which may be configured to non-invasively measure one or more analytes in blood circulating in subsurface vasculature proximate to the wearable device. In a non-exhaustive list, the measurement platform 330 may include any one of an acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the measurement platform 330 may be miniaturized so that the wearable device may be worn on the body without significantly interfering with the wearer's usual activities.

In some examples, the measurement platform 330 may further include one or more additional signal sources, each of which may transmit an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the nanoparticle conjugates.

The wearable device 300 may also include a user interface 360 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 360 may include a display 362 where a visual indication of the alert or recommendation may be displayed.

Figure 4:
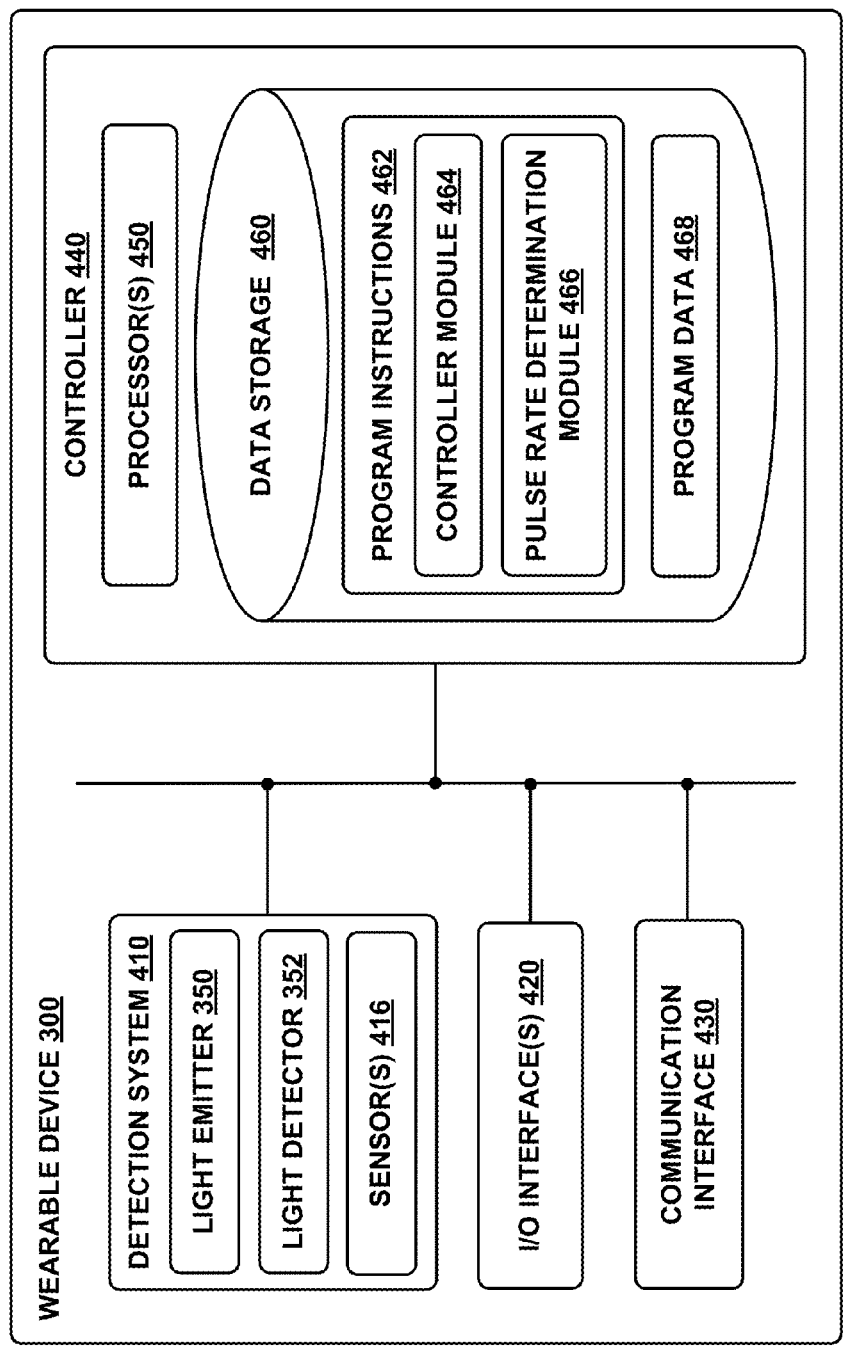
FIG. 4 is a functional block diagram of components disposed in an example wearable electronic device.

FIG. 4 is a simplified block diagram illustrating example components of the wearable device 300. In the illustrated example, the wearable device 300 includes a detection system 410, an input/output (I/O) interface 420, a communication interface 430 for transmitting data to a remote system, and a controller 440.

The controller 440 may be provided as a computing device that includes one or more processors 450. The one or more processors 450 can be configured to execute computer-readable program instructions 470 that are stored in the data storage 460 and that are executable to provide the functionality of a wearable device 300 described herein.

The data storage 460 may include or take the form of one or more non-transitory, computer-readable storage media that can be read or accessed by at least one processor 450. The one or more computer-readable storage media can include volatile and/or non-volatile storage components, such as optical, magnetic, organic or other memory or disc storage, which can be integrated in whole or in part with at least one of the one or more processors 450. In some embodiments, the computer readable data storage 460 can be implemented using a single physical device (e.g., one optical, magnetic, organic or other memory or disc storage unit), while in other embodiments, the computer readable data storage 460 can be implemented using two or more physical devices.

The detection system 410 includes the light emitter 350, the light detector 352, and one or more sensors 416. In line with the description above, the light emitter 350 is configured to emit illumination into an environment of interest (e.g., into a portion of subsurface vasculature), and light detector 352 is configured to detect one or more properties of light emitted from the portion of subsurface vasculature in response to illumination emitted from the light emitter 352. In a non-exhaustive list, the light detector 352 may include one or more of a photodiode, a phototransistor, a photoresistor, an active pixel sensor, a CCD, a camera, a spectrometer, an interferometer, or some other light sensitive element configured to detect one or more properties of the emitted light.

The detection system 410 could additionally include electronics configured to operate the light emitter 350 and the light detector 352. The electronics could include a high-speed analog-to-digital converter (ADC) configured to sample an output (e.g., a voltage, a current) of one or more light-sensitive elements of the light detector 352. Additionally or alternatively, the electronics could include analog frontend circuitry that includes analog circuitry configured to filter, decimate, quantize, or otherwise alter and/or perform other analog operations or computations on the output(s) of the light detector 352 to produce an output electronic signal that is related to physiological properties or other parameters in the environment. This output electronic signal(s) could then be used (e.g., sampled by an ADC of a microcontroller) to determine the cardiovascular pulse rate of a wearer.

The detection system 410 may additionally include one or more sensors 416 for detecting additional or alternative properties of the environment of interest (e.g., for detecting physiological parameters of a human whose body includes the environment of interest). Such additional detected properties could include any physiological parameters that may relate to the health of the person whose biological tissues are being measured by the wearable device 300. For example, the detection system 410 could include detectors configured to measure blood pressure, respiration rate, skin temperature, galvanic skin response, etc. In a non-exhaustive list, the one or more sensors 416 may include any one of an optical sensor, an acoustic sensor, an electrochemical sensor, a thermal sensor, a mechanical sensor, a magnetic sensor, and/or an electromagnetic sensor.

The one or more sensors 416 may include one or more devices for measuring one or more non-physiological parameters. By way of example, the one or more sensors 416 may include an IMU, which may itself include one or more accelerometers, gyrometers, and/or magnetometers. The IMU may measure a velocity and/or an acceleration of the wearable device in one or more dimensions, from which the IMU (or the one or more processors 450) may determine a movement of the wearable device. In another example, the one or more sensors 416 may include a microphone. Note that the microphone could also be a component of the I/O interface 420.

The program instructions 462 stored on the data storage 460 may include instructions to perform any of the methods described herein. For instance, in the illustrated embodiment, program instructions 462 include a controller module 464 and a pulse rate determination module 466.

The controller module 464 can include instructions for operating the detection system 410, for example, the light emitter 350 and the light detector 352. For example, the controller module 464 may operate the light emitter 350 and the light detector 414 at a plurality of points in time to obtain a respective plurality of samples of a PPG signal. In particular, the controller module 464 can include instructions for operating the light emitter 350 to emit illumination into a target environment (e.g., tissue of a person) and for controlling the light detector 352 to detect an intensity, a wavelength, and/or other properties of light emitted from the environment responsive to the illumination.

The controller module 464 can also include instructions for operating the I/O interface 420. For example, the controller module 464 may include instructions for displaying data collected by the detection system 410 and analyzed by the pulse rate determination module 466. Further, the controller module 464 may include instructions to execute certain functions based on inputs accepted by the I/O interface 420, such as inputs accepted by one or more buttons or touchscreen displays disposed on the user interface.

The pulse rate determination module 466 may include instructions for receiving data from and/or operating the detection system 410, analyzing the data to determine pulse and/or respiration rates, identifying potential respiratory or other health conditions that the user may suffer from based on at least the determined respiration rate, or other analytical processes relating to the environment proximate to the wearable device 300.

Some of the program instructions of the controller module 464 and the pulse rate determination module 466 may, in some examples, be stored in a computer-readable medium and executed by a processor located external to the wearable device 300. For example, the wearable device 300 could be configured to illuminate and to receive light from portion of biological tissue (or to otherwise generate or obtain a plurality of samples of a signal of interest) and then transmit related data to a remote server, which may include a mobile device, a personal computer, the cloud, or any other remote system, for further processing (e.g., for the determination of pulse rates and/or frequencies of oscillating patterns in the received light using methods described herein).

I/O interface 420 could include indicators, displays, buttons, touchscreens, head-mounted displays, microphones, and/or other elements configured to present information about the wearable device 300 to a user and/or to allow the user to operate the wearable device 300. Additionally or alternatively, the wearable device 300 could be configured to communicate with another system (e.g., a cellphone, a tablet, a computer, a remote server) and to present elements of a user interface using the remote system. The I/O interface 420 could be configured to allow a user to specify some operation, function, or property of operation of the wearable device 300. The I/O interface 420 could be configured to present a determined pulse rate of blood in a portion of subsurface vasculature or some other health state of a wearer of the wearable device 300, or to present some other information to a user. Other configurations and methods of operation of the I/O interface 420 are anticipated.

Communication interface 430 may also be operated by instructions within the program instructions 462, such as instructions for sending and/or receiving information via a wireless antenna, which may be disposed on or in the wearable device 300. The communication interface 430 can optionally include one or more oscillators, mixers, frequency injectors, etc. to modulate and/or demodulate information on a carrier frequency to be transmitted and/or received by the antenna. In some examples, the wearable device 300 is configured to indicate an output from the controller 440 by transmitting an electromagnetic or other wireless signal according to one or more wireless communications standards (e.g., Bluetooth®, WiFi®, IRdA®, ZigBee®, WiMAX®, LTE®). In some examples, the communication interface 430 could include one or more wired communications interfaces and the wearable device 300 could be configured to indicate an output from the controller 440 by operating the one or more wired communications interfaces according to one or more wired communications standards (e.g., USB, FireWire, Ethernet, RS-232).

The data storage 460 may further contain other data or information, such as scattering, absorption, or other optical properties of tissues of a user of the wearable device 300, that may be useful in determining pulse rates or other physiological parameters. Further, the data storage 460 may contain data corresponding to pulse rate transition probabilities or other property baselines that describe expected changes in cardiovascular pulse rate or other properties of biological tissues and/or of a body. The baselines may be pre-stored on the data storage 460, may be transmitted from a remote source, such as a remote server, or may be generated by the pulse rate determination module 466 itself. The pulse rate determination module 466 may include instructions for generating individual baselines for the user of the wearable device 300 based on data collected over a certain period of time. For example, the pulse rate determination module 466 may generate a baseline set of transition probabilities or other statistics describing expected changes in pulse rate over time based on cardiovascular pulse determined based on PPG signals detected from portions of subsurface vasculature. The pulse rate determination module 466 could store those baselines in the data storage 460 for later use (e.g., to apply a forward-backward filter to a set of determined pulse rates or to perform some other filtering or determination related to a cardiovascular pulse). Baselines may also be generated by a remote server and transmitted to the wearable device 300 via the communication interface 430.

In some examples, obtained samples of a PPG signal or other physiological property or parameter of interest, determined pulse rates, or other information generated by the wearable device 300 may additionally be input to a cloud network and be made available for download by a user's physician. Analyses may also be performed on the collected data, such as estimates of pulse rate variability, arrhythmia, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

Figure 5A:
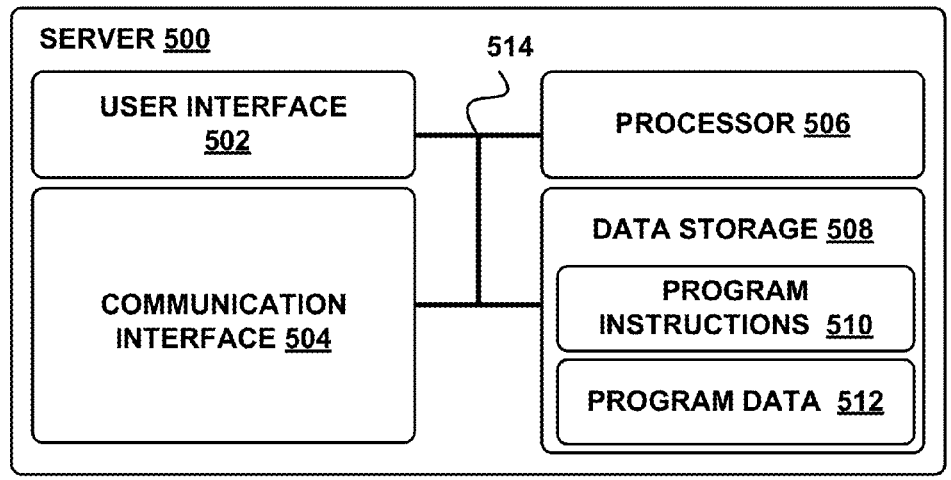
FIG. 5A is a block diagram of an example server.

Turning now to FIG. 5A, a block diagram of a server in accordance with an example embodiment is shown. In particular, server 500 shown in FIG. 5A can be configured to perform one or more functions of server 230 and/or server data storage 232. Server 500 may include a user interface 502, a communication interface 504, a processor 506, and/or data storage 508, all of which may be linked together via a system bus, network, or other connection mechanism 514.

The user interface 502 may include user input devices such as a keyboard, a keypad, a touch screen, a computer mouse, a track ball, a joystick, and/or other similar devices, now known or later developed. The user interface 502 may also include user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. Additionally, the user interface 502 may be configured to generate audible output(s), via a speaker, speaker jack, audio output port, audio output device, earphones, and/or other similar devices, now known or later developed. In some embodiments, the user interface 502 may include software, circuitry, or another form of logic that can transmit data to and/or receive data from external user input/output devices.

The communication interface 504 may include one or more wireless interfaces and/or wireline interfaces that are configurable to communicate via a network, such as network 220 shown in FIG. 2. The wireless interfaces, if present, may include one or more wireless transceivers, such as a BLUETOOTH® transceiver, a WiFi® transceiver perhaps operating in accordance with an IEEE 802.11 standard (e.g., 802.11b, 802.11g, 802.11n), a WiMAX transceiver perhaps operating in accordance with an IEEE 802.16 standard, a Long-Term Evolution (LTE) transceiver perhaps operating in accordance with a 3rd Generation Partnership Project (3GPP) standard, and/or other types of wireless transceivers configurable to communicate via local-area or wide-area wireless networks. The wireline interfaces, if present, may include one or more wireline transceivers, such as an Ethernet transceiver, a Universal Serial Bus (USB) transceiver, or similar transceiver configurable to communicate via a twisted pair wire, a coaxial cable, a fiber-optic link or other physical connection to a wireline device or network. Other examples of wireless and wireline interfaces may exist as well.

The processor 506 may include one or more general purpose processors (e.g., microprocessors) and/or one or more special purpose processors (e.g., digital signal processors (DSPs), graphical processing units (GPUs), floating point processing units (FPUs), network processors, or application specific integrated circuits (ASICs)). The processor 506 may be configured to execute computer-readable program instructions 510 that are contained in data storage 508, and/or other instructions, to carry out various functions described herein.

Thus, the data storage 508 may include one or more non-transitory computer-readable storage media that can be read or accessed by the processor 506. The one or more computer-readable storage media may include volatile and/or non-volatile storage components, such as optical, magnetic, organic or other memory or disc storage, which can be integrated in whole or in part with the processor 506. In some embodiments, the data storage 508 may be implemented using a single physical device (e.g., one optical, magnetic, organic or other memory or disc storage unit), while in other embodiments, the data storage 508 may be implemented using two or more physical devices.

Data storage 508 may also include the program data 512 that can be used by processor 506 to carry out functions described herein. In some embodiments, the data storage 508 may include, or have access to, additional data storage components or devices (e.g., cluster data storages described below).

Figure 5B:
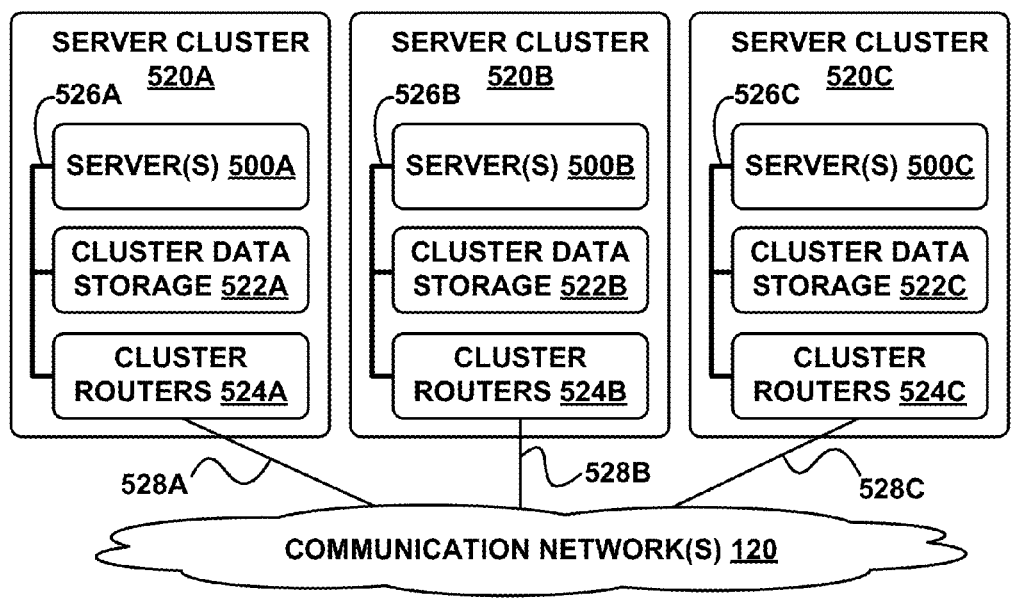
FIG. 5B is a block diagram of an example cloud-based server system.

FIG. 5B depicts a cloud-based server in accordance with an example embodiment. In FIG. 5B, functions of server 230 and server data storage device 232 may be distributed among three server clusters 520A, 520B, and 520C. Server cluster 520A may include one or more servers 500A, cluster data storage 522A, and cluster routers 524A connected by a local cluster network 526A. Similarly, server cluster 520B may include one or more servers 500B, cluster data storage 522B, and cluster routers 524B connected by a local cluster network 526B. Likewise, server cluster 520C may include one or more servers 500C, cluster data storage 522C, and cluster routers 524C connected by a local cluster network 526C. Servers 520A, 520B, and 520C may communicate with network 220 via communication links 528A, 528B, and 528C, respectively.

In some embodiments, each of the server clusters 520A, 520B, and 520C may have an equal number of servers, an equal number of cluster data storages, and an equal number of cluster routers. In other embodiments, however, some or all of the server clusters 520A, 520B, and 520C may have different numbers of servers, different numbers of cluster data storages, and/or different numbers of cluster routers. The number of servers, cluster data storages, and cluster routers in each server may depend on the computing task(s) and/or applications assigned to each server.

In the server cluster 520A, for example, server 500A can be configured to perform various computing tasks of server 230. In one embodiment, these computing tasks can be distributed among one or more of servers 500A. Servers 500B and 500C in server clusters 520B and 520C may be configured the same or similarly to server 500A in server cluster 520A. On the other hand, in some embodiments, server clusters 500A, 500B, and 500C each may be configured to perform different functions. For example, server cluster 500A may be configured to perform one or more functions of server 230, and server clusters 500B and server 500C may be configured to perform functions of one or more other servers. Similarly, the functions of server data storage device 232 can be dedicated to a single server cluster, or spread across multiple server clusters.

Cluster data storages 522A, 522B, and 522C of the servers 520A, 520B, and 520C, respectively, may be data storage arrays that include disk array controllers configured to manage read and write access to groups of hard disk drives. The disk array controllers, alone or in conjunction with their respective servers, may also be configured to manage backup or redundant copies of the data stored in cluster data storages to protect against disk drive failures or other types of failures that prevent one or more servers from accessing one or more cluster data storages.

Similar to the manner in which the functions of server 230 and server data storage device 232 can be distributed across server clusters 520A, 520B, and 520C, various active portions and/or backup/redundant portions of these components can be distributed across cluster data storages 522A, 522B, and 522C. For example, some cluster data storages 522A, 522B, and 522C may be configured to store backup versions of data stored in other cluster data storages 522A, 522B, and 522C.

Cluster routers 524A, 524B, and 524C in servers 520A, 520B, and 520C, respectively, may include networking equipment configured to provide internal and external communications for the servers. For example, cluster routers 524A in server 520A may include one or more packet-switching and/or routing devices configured to provide (i) network communications between servers 500A and cluster data storage 522A via cluster network 526A, and/or (ii) network communications between the server cluster 520A and other devices via communication link 528A to communication network 220. Cluster routers 524B and 524C may include network equipment similar to cluster routers 524A, and cluster routers 524B and 524C may perform networking functions for server clusters 520B and 520C that cluster routers 524A perform for server cluster 520A.

Additionally, the configuration of cluster routers 524A, 524B, and 524C can be based at least in part on the data communication requirements of the servers and cluster storage arrays, the data communications capabilities of the network equipment in the cluster routers 524A, 524B, and 524C, the latency and throughput of the local cluster networks 526A, 526B, 526C, the latency, throughput, and cost of the wide area network connections 528A, 528B, and 528C, and/or other factors that may contribute to the cost, speed, fault-tolerance, resiliency, efficiency and/or other design goals of the system architecture.

III. EXAMPLE METHODS

Figure 6:
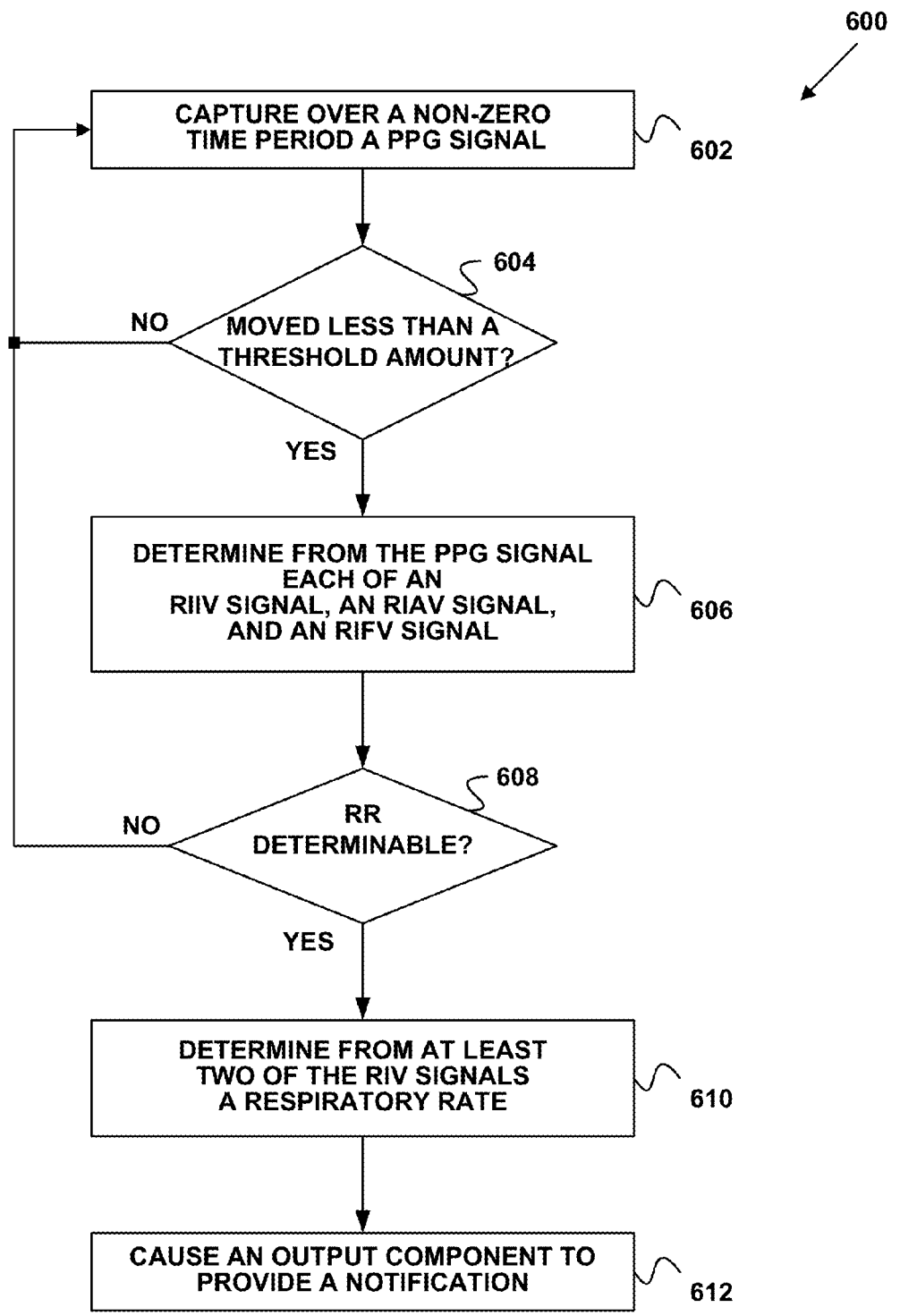
FIG. 6 is a flowchart of an example method.

Turning now to FIG. 6, a flow diagram of an example method 600 is shown. A component of a health monitoring system, such one or more of the wearable devices and/or servers described herein, may implement the functions of the method 600 to determine a respiration rate for one or more users of one of the wearable devices. Alternatively, multiple components of the health monitoring system may implement the functions of the method 600. Functions described in blocks of the flowchart may be provided as instructions stored on a non-transitory computer readable medium that can be executed by a computing system to perform the functions.

In one example, a user of a wearable device may initiate the method 600 by interacting with a user interface component of the wearable device. In another example, the wearable device may automatically initiate the method 600 at specific times. For instance, the wearable device may perform one or more steps of the method 600 at specific times of day or after an interval of time has elapsed from the last performance of the method 600. Additionally or alternatively, the wearable device could perform the method 600 after capturing a non-physiological parameter. By way of example, the wearable device may automatically perform one or more functions the method 600 upon determining that the wearable device has moved less than a threshold amount.

Beginning at block 602, the method 600 includes capturing by a wearable device over a non-zero time period a PPG signal. The non-zero time period may be about 20 seconds, though longer or shorter time periods are possible as well. At block 604, the method 600 includes a first decision point at which a first determination is made as to whether the wearable device during the capture of the PPG signal has moved less than a threshold amount. The wearable device may make the first determination based on data received during the non-zero time period from a sensor included in the wearable device that is configured to capture a movement of the wearable device, such as an IMU. In line with the above discussion, making the first determination may improve the reliability of determined respiration rates, as movements of the wearable device during the non-zero time period could distort the PPG signal and/or could introduce variations in the PPG signal that are similar to RIVs. Determining that the wearable device has moved less than the threshold amount (e.g., a movement in any given direction is less than about 1 centimeter) may indicate that the wearable device is substantially stationary, in which case any variations in the PPGs signal are likely due to RIVs.

If the first determination is that wearable device has not moved less than the threshold amount, then the method 600 includes returning to block 602. In some examples, the wearable device may output a notification responsive to the first determination being that the wearable device has not moved less than the threshold amount. For instance, the notification may be a visual message and/or an audio message indicating that the wearable device cannot determine the user's respiration rate. Further, the visual/audio message may include a request that the user minimize movement of the wearable device to facilitate determination of the respiration rate.

In some examples, the wearable device may not automatically capture another PPG signal upon returning to block 602. Instead, the wearable device may wait for a particular condition to occur before returning to block 602, such as an interaction received from a user input device, an amount of time elapsing from the last PPG signal being captured, or an indication that over another non-zero time period the wearable device has moved less than the threshold amount (e.g., indicating that the wearable device is substantially stationary).

On the other hand, if the first determination is that the wearable device has moved less than the threshold amount, then the method 600 continues at block 606 with determining from the PPG signal each of an RIIV signal, an RIAV signal, and an RIFV signal. Next at block 608, the method 600 includes a second decision point. Here, a second determination is made as to whether a respiration rate (RR) is determinable. In some instances, differences in the RIV signals may render unreliable a respiration rate determined from the RIV signals. Making the second determination may thus serve as an additional safeguard against providing the user (or a medical professional, for instance) with an unreliable respiration rate.

Figure 7:
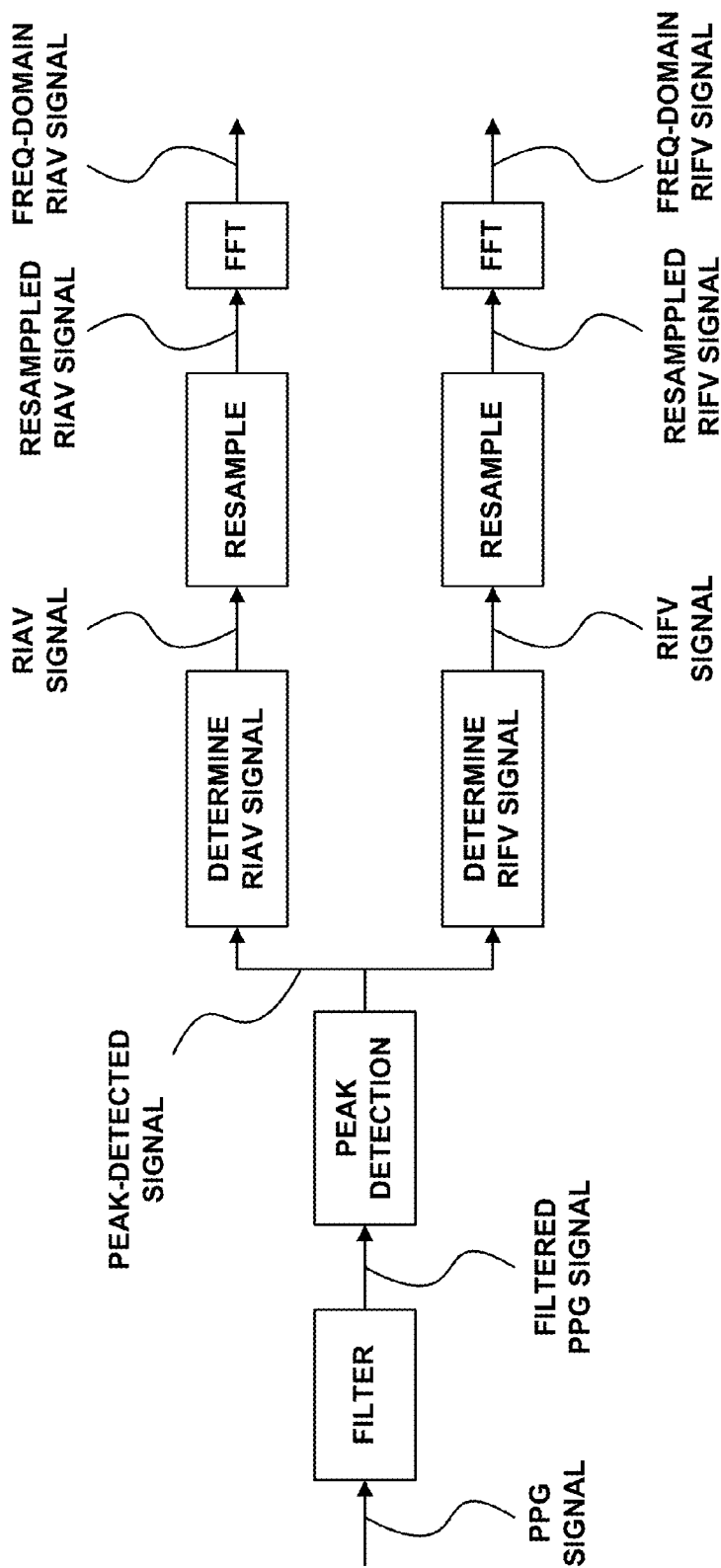
FIG. 7 is a flowchart showing operations used to determine example frequency-domain respiratory-induced variations in a photoplethysmographic signal.

In one example, the wearable device may make the second determination. By way of example, the wearable device may make the second determination based on a plurality of preliminary respiration rates. By way of example, the plurality of preliminary respiration rates includes a preliminary respiration rate determined from at least RIV signals. In order to make the second determination, the wearable device may first determine a frequency-domain signal from each of the RIIV signal, the RIAV signal, and the RIFV signal. FIG. 7 shows a flowchart for determining frequency-domain RIV signals.

As shown, the wearable device may provide a filtered PPG signal by filtering a PPG signal with a band-pass filter. A lower cutoff frequency of the band-pass filter may remove from the PPG signal a DC component, while an upper cutoff frequency may remove noise that can adversely affect determination of the RIAV signal and the RIFV signal. By way of example, the lower cutoff frequency may be about 0.35 Hertz, and the upper cutoff frequency may be about 3 Hertz, though other upper and/or lower cutoff frequencies may also be used.

Figure 8A:
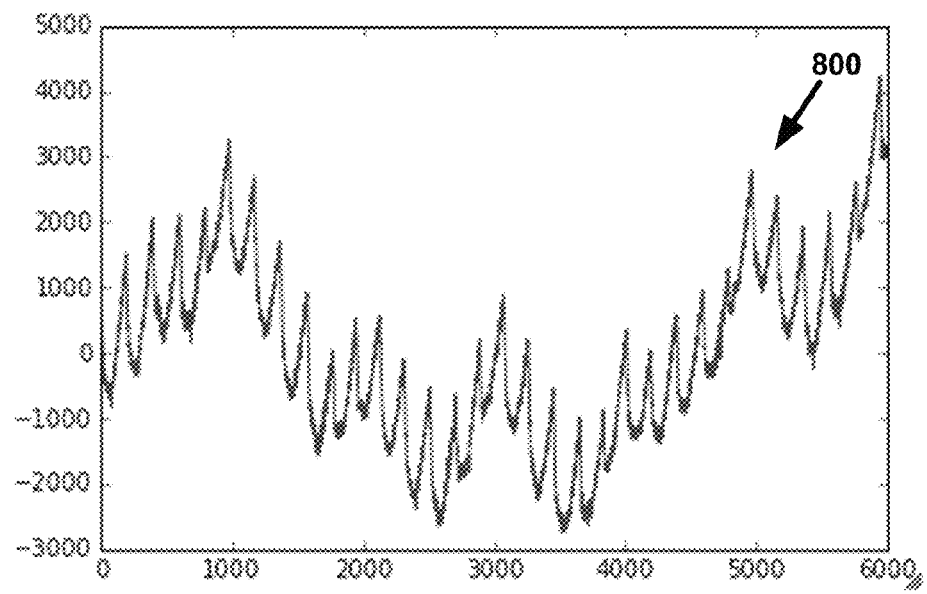
FIGS. 8A, 8B, 8C, 8D, and 8E are graphs of example signals.
Figure 8B:
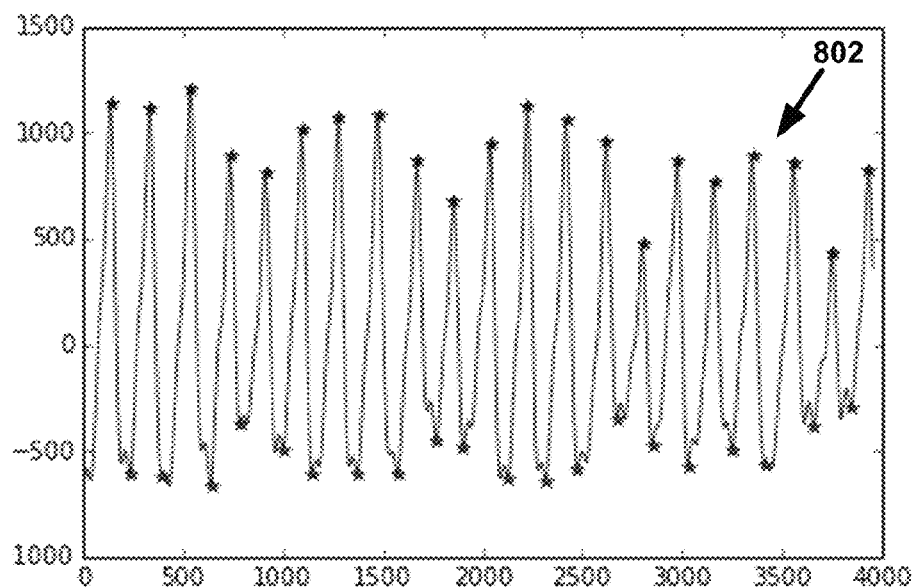

Next, the wearable device may perform a peak detection algorithm to determine a value for each maximum and minimum value of the PPG signal, thereby providing a peak-detected signal. The wearable device may use any method, algorithm, or process now known or later developed that is suitable for identifying peaks in periodic or quasi-periodic signals. By way of example, FIG. 8A shows an example PPG signal 800, and FIG. 8B shows an example peak-detected signal 802.

Figure 8C:
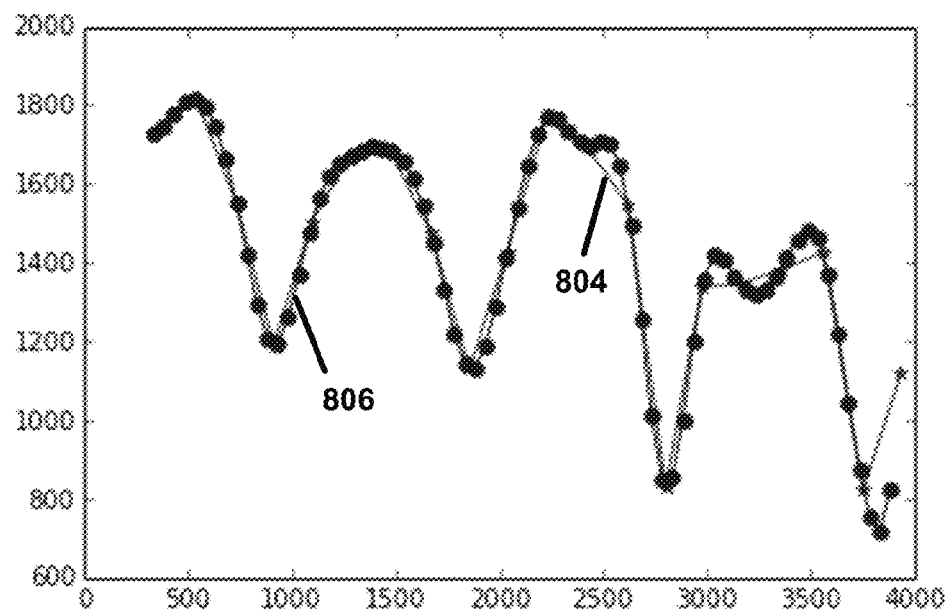
Figure 8D:
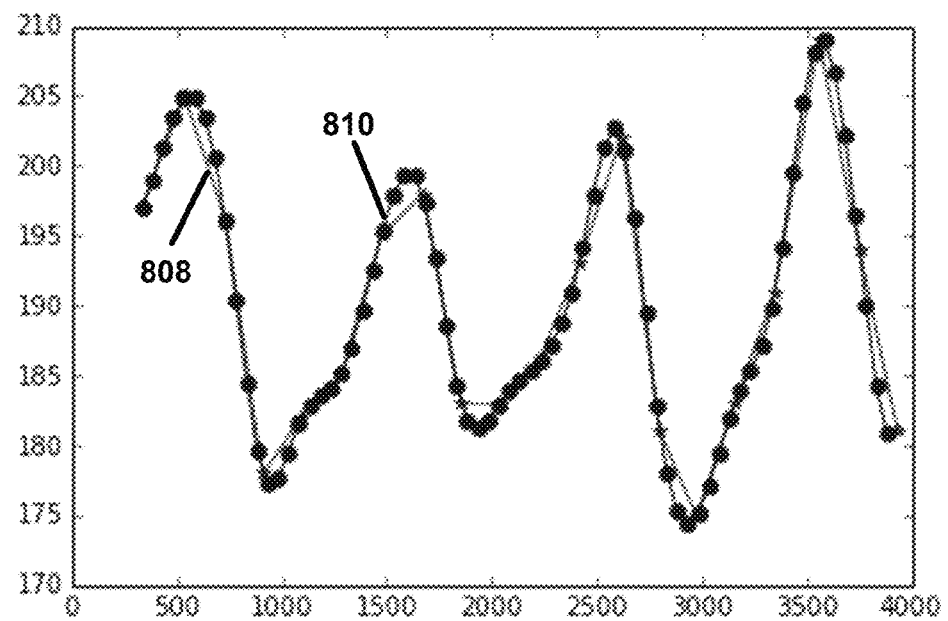

From the peak-detected signal, the wearable device may determine an RIAV signal by calculating an amplitude of each pulse (e.g., maximum minus minimum), while determining the RIFV signal by determining the time between each pulse (e.g., peak to peak) of the PPG signal. The wearable device may next resample each of the RIAV signal and the RIFV signal to provide a resampled RIAV signal and a resampled RIFV signal, respectively. As one non-limiting example, the wearable device may perform the resampling by using any suitable linear interpolation method to resample on a 4 Hertz grid each of the RIAV signal and the RIFV signal. FIG. 8C shows an example RIAV signal 804 and a resampled RIAV signal 806, while FIG. 8D shows an example RIFV signal 808 and a resampled RIFV signal 810. Note that the dots on shown on the resampled signals 804, 808 correspond to a point determined by linear interpolation. In some examples, the wearable device may use a different grid for linear interpolation (e.g., a frequency other than 4 Hertz), or a different resampling technique may be used. The wearable device may then determine a frequency-domain RIAV signal and a frequency-domain RIFV signal by performing a fast Fourier transform (FFT) on the resampled RIAV signal and the resampled RIFV signal, respectively.

With respect to the RIIV signal, the wearable device may determine that the PPG signal is the RIIV signal. In this example, the wearable device may determine a frequency-domain RIIV signal by performing an FFT on the PPG signal. Note that in some examples, the wearable device may determine the RIIV signal by filtering the PPG signal and/or by resampling the PPG signal prior to determining the FFT of the RIIV signal. By way of example, the wearable device may use linear interpolation to resample the PPG signal on a 4 Hertz grid, though another resampling frequency and/or grid may be used as well. Note that the same resampling technique (and frequency grid) should be used to resample each RIV signal when the wearable device performs such resampling.

Figure 8E:
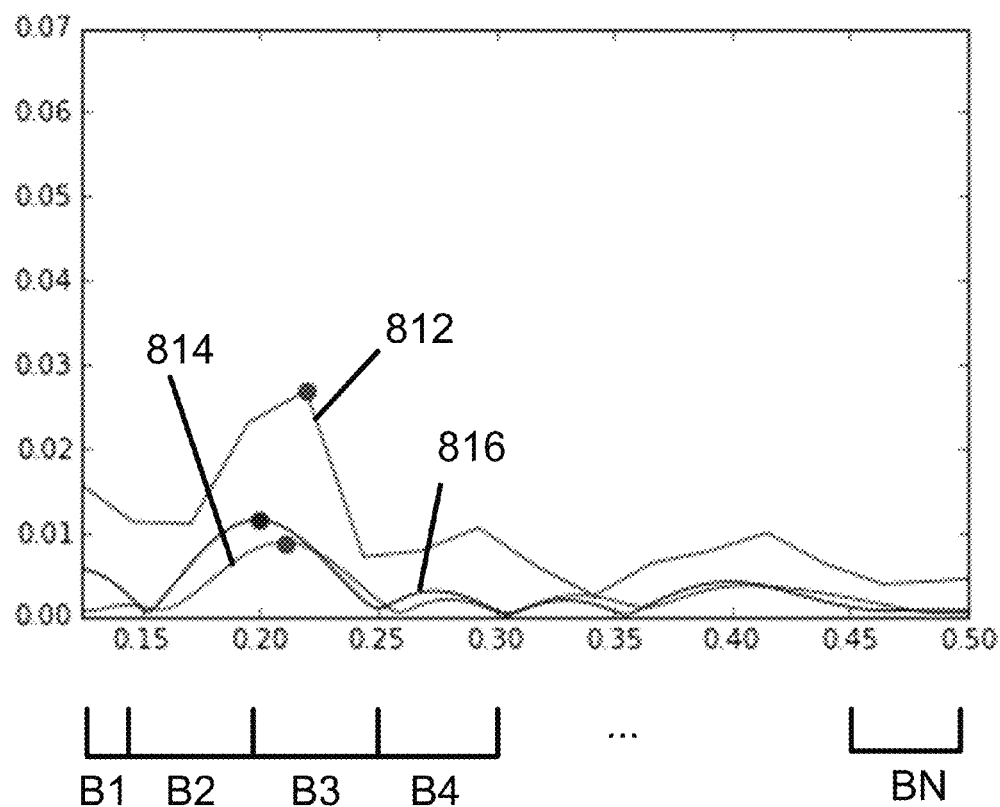

The wearable device may determine the preliminary respiration rates by identifying peaks in the frequency-domain RIV signals that are within a range of respiratory frequencies, e.g., between 0 and 1 Hertz. By way of example, FIG. 8E shows a graph of example frequency-domain RIV signals. As shown, a frequency-domain RIIV signal 812 may have a peak at about 0.23 Hertz (i.e., breaths per second), a frequency-domain RIFV signal 814 may have a peak at about 0.20 Hertz, and a frequency-domain RIAV signal 816 may have a peak at about 0.21 Hertz. Thus, the wearable device may determine from the preliminary respiration rate for each of the frequency-domain RIV signals 812, 814, and 816 as being 0.23 Hertz, 0.20 Hertz, and 0.21 Hertz, respectively.

In one example, the wearable device may make the second determination when at least two of the preliminary respiration rates are within a predetermined threshold of each other (e.g., the difference between any two preliminary respiration rates is within than a predetermined threshold difference). Alternatively, the wearable device may make the second determination when all of the preliminary respiration rates are within a predetermined threshold to each other (e.g., the difference between the highest preliminary respiration rate and the lowest preliminary respiration is within a predetermined threshold difference). In each of these examples, the value of the predetermined threshold may depend on the desired correspondence between the preliminary respiration rates. As a non-limiting example, the predetermined threshold could be between about 0.1 Hertz and about 1 Hertz.

Alternatively, a server connected to the wearable device via a wired or wireless connection may make the second determination. Here, the wearable device may generate a vector that includes data indicative of an energy in each of N frequency bins for each frequency-domain RIV signal, which are shown in FIG. 8E. Here, the resulting vector $V_{RIV}$ can be represented as follows:

$$V_{RIV}=[E_{RIIV-B1}, \ldots ,E_{RIAV-BN}, E_{RIAV-B1}, \ldots , E_{RIAV-BN}, E_{RIFV-B1}, \ldots ,E_{RIFV-BN}]$$

where each value of E is an energy of an RIV signal in one of bins B1-BN. For each frequency-domain RIV signal, the energy E in a given bin may be an average energy, a maximum energy, a minimum energy, or some other statistic of the energy in the bin. In one example, the server may determine the vector $V_{RIV}$, in which case the wearable device may digitize the PPG signal and send the PPG signal to the server. The server may determine the vector from the received PPG signal, perhaps by performing the functions described with respect to FIG. 7. In any event, the server may use a machine-learning algorithm to make the second determination based on the vector $V_{RIV}$. For instance, if the machine-learning algorithm uses a KNN-regression, then the server may make the second determination based on the k nearest neighbors in a database to the vector $V_{RIV}$. As noted above, the value of k may depend on the size of the database accessed by the machine-learning algorithm, as well as other factors such as the amount of time needed to make the determination, processing resources, etc.

Returning to FIG. 6, if the second determination is that the respiration rate is not determinable, then the method 600 includes returning to block 602 in a similar manner as described with respect to the first determination being that the wearable device has not moved less than the predetermined amount.

On the other hand, if the second determination is that the respiration rate is determinable, then the method 600 includes determining the respiration rate at block 610. In some examples, the wearable device may perform the functions of block 610 by combining two or more preliminary respiration rates. To this end, the wearable device may average the preliminary respiration rates, or the wearable device may average the preliminary respiration rates that are within a predetermined threshold of each other. In the latter case, the wearable device may omit from the average a preliminary respiration rate that is not within the predetermined threshold from the other preliminary respiration rates. As another example, the wearable device may determine a cross-correlation of two or more frequency-domain RIV signals, thereby providing a cross-correlated signal. Here, a peak in the cross-correlated signal between 0 Hertz and 1 Hertz may be correlated to the respiration rate. And in yet other examples, the wearable device may determine that the respiration rate is one of a minimum preliminary respiration rate, a maximum preliminary respiration rate, or a median preliminary respiration rate.

In other examples, the server may perform the functions of block 610. Here, the server may use the machine-learning algorithm to determine from the vector $R_{RIV}$ the respiration rate, and the server may send to the wearable device data indicative of the determined respiration rate. Alternatively, the server may determine the respiration rate by employing any of the operations described in the examples in which the wearable device performs the functions of block 610.

At block 612, the method 600 includes the wearable device causing an output device to provide a notification. By way of example, the wearable device may cause an output component of a user interface device to provide an audio or visual notification. In this case, the wearable device may convert the determined respiration rate from breaths per second to breaths per minute. In the example described with respect to FIG. 8E, for instance, the wearable device may determine that the respiration rate is about 12.6 breaths per minute.

In another example, the notification may alert the user of the presence of symptoms indicative of the user potentially having a respiratory condition. In this case, the wearable device may use other physiological and non-physiological data to determine whether the respiration rate may be a symptom of a medical condition. For instance, the wearable device may receive from one sensor data indicative of the user's body temperature, and the wearable device may also receive data from another sensor indicative of the user's activity level (e.g., whether the user has been running or been sedentary over a period of time preceding the capture of the PPG signal). Moreover, the wearable device may store in a data storage data indicative of a number of previous, consecutively determined respiration rates and temporally associated physiological and non-physiological parameters. Rather than provide a notification of a potential illness based on one determined respiration rate, the wearable device may first determine whether a trend in respiration rates, physiological parameters, and non-physiological parameters over a longer period of time (perhaps several dozen sets of data taken over minutes, hours, days, etc.) is indicative of the user potentially suffering from an illness. If the trend is indicative of the user suffering from a respiratory illness, then the notification may alert the user of the potential illness and possibly advise the user to consult a medical professional.

Further, the wearable device may send a message to a computing device operated by a physician (or other medical professional) alerting the physician of the user potentially suffering from an illness. The message may be an email, a text message, an instant message, or the like that includes data indicative of the physiological data (included the determined respiration rate(s)) and non-physiological data used by the wearable device to determine that the user might have a respiratory illness. In this manner, the physician may follow up with the user to schedule an appointment, or perhaps direct the user to seek immediate medical attention, depending on the physician's assessment of data.

IV. CONCLUSION

Where example embodiments involve information related to a person or a device of a person, the embodiments should be understood to include privacy controls. Such privacy controls include, at least, anonymization of device identifiers, transparency, and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the figures should not be viewed as limiting. It should be understood that other embodiments may include more or less of each element shown in a given figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device comprising:
   a sensor configured to capture photoplethysmographic (PPG) signals;
   a processor;
   a communication interface, wherein the communication interface is configured to connect the wearable device to a remote computing device; and
   a controller, configured to:
      (i) receive from the sensor over a non-zero time period a PPG signal;
      (ii) make a first determination that, during the non-zero time period, the wearable device has moved less than a threshold amount;
      (iii) in response to the first determination that, during the non-zero time period, the wearable device has moved less than the threshold amount, determine from the PPG signal each of (1) a respiratory-induced intensity variation (RIIV) signal, (2) a respiratory-induced amplitude variation (RIAV) signal, and (3) a respiratory-induced frequency variation (RIFV) signal;
      (iv) determine in each of a plurality of frequency bins a power level of each of the RIIV signal, the RIAV signal, and the RIFV signal;
      (v) send to the remote computing device via the communication interface data indicative of each determined power level;
      (vi) receive from the remote computing device via the communication interface a signal that includes data indicative of whether the respiration rate is determinable; and
      (vii) if the signal indicates that the respiration rate is determinable, determine a respiration rate based on at least two of the RIIV signal, the RIAV signal, and the RIFV signal.

2. The wearable device of claim 1, wherein the controller is further configured to determine a plurality of preliminary respiration rates, wherein each preliminary respiration is based on at least one of the RIIV signal, the RIAV signal, and the RIFV signal.

3. The wearable device of claim 2, wherein determining the plurality of preliminary respiration rates comprises identifying a peak in at least one of the RIIV signal, the RIAV signal, or the RIFV signal, wherein a frequency of each identified peak is within a range of respiration frequencies.

4. The wearable device of claim 2, wherein determining the respiration rate comprises combining at least two preliminary respiration rates that are within a threshold of each other.

5. The wearable device of claim 2, wherein determining the respiration rate comprises combining all of the preliminary respiration rates.

6. The wearable device of claim 2, wherein determining the preliminary respiration rate from each of the RIIV signal, the RIAV signal, and the RIFV signal comprises identifying a peak in the respective respiratory-induced signal in a range of respiration frequencies.

7. The wearable device of claim 1, wherein the controller is further configured to
   generate a vector that includes each determined power level and wherein sending data to the remote computing device indicative of each determined power level comprises sending the vector.

8. The wearable device of claim 1, further comprising an output component to provide a notification, wherein the controller is further configured to provide the notification, and wherein the notification is based on the determined respiration rate.

9. The wearable device of claim 8, wherein the notification includes at least one of a visual output or an auditory output.

10. The wearable device of claim 1, wherein the sensor comprises a light emitter and a light detector.

11. The wearable device of claim 1, further comprising:
a mount, wherein the mount secures the device to an external body surface.

12. The wearable device of claim 11, wherein the external body surface is a location on a wrist.

13. The wearable device of claim 11, wherein the mount comprises a band that can enclose the wrist.

14. The wearable device of claim 11, wherein the mount comprises an adhesive substrate.

15. The wearable device of claim 1, further comprising:
a user interface, wherein the controller is further configured to cause the user interface to indicate information relating to the determined respiration rate.

16. The wearable device of claim 15, wherein the user interface comprises a display.

17. The wearable device of claim 1, further comprising a second sensor configured to capture movement data of the wearable device, and wherein the controller is further configured to:
receive, from the second sensor and over the non-zero time period, movement data of the wearable device.

18. The wearable device of claim 17, wherein the second sensor comprises one or more accelerometers, gyrometers, and/or magnetometers.

* * * * *